US005612622A

United States Patent [19]
Goldman et al.

[11] Patent Number: 5,612,622
[45] Date of Patent: Mar. 18, 1997

[54] APPARATUS FOR IDENTIFYING PARTICULAR ENTITIES IN A LIQUID USING ELECTRICAL CONDUCTIVITY CHARACTERISTICS

[75] Inventors: Don S. Goldman; Steven Wilcox, both of Folsom, Calif.

[73] Assignee: Optical Solutions, Inc., Folsom, Calif.

[21] Appl. No.: 365,908

[22] Filed: Dec. 28, 1994

[51] Int. Cl.$^6$ .................................................. G01N 27/42
[52] U.S. Cl. ........................ 324/444; 324/676; 324/672; 204/400
[58] Field of Search .................................. 324/439, 444, 324/445, 446, 449, 450, 663, 664, 674, 686, 689, 672, 690, 676, 678; 73/61.41, 61.43, 61.44, 304 C; 204/400

[56] References Cited

U.S. PATENT DOCUMENTS

| | | | |
|---|---|---|---|
| 3,155,898 | 11/1964 | Chape | 324/674 X |
| 3,233,173 | 2/1966 | Lees et al. | 324/663 |
| 3,774,238 | 11/1973 | Hardway | 324/61 |
| 4,074,184 | 2/1978 | Dechene et al. | 324/30 |
| 4,227,151 | 10/1980 | Ellis et al. | 324/448 |
| 4,590,431 | 5/1986 | Anderson et al. | 324/445 X |
| 4,896,099 | 1/1990 | Suzuki | 324/689 X |
| 4,899,101 | 2/1990 | Porges | 324/663 |
| 4,924,702 | 5/1990 | Park | 73/304 |
| 4,928,065 | 5/1990 | Lane et al. | 324/464 |
| 4,935,207 | 6/1990 | Stanbro et al. | 422/68.1 |
| 5,068,617 | 11/1991 | Reich | 324/663 |
| 5,187,444 | 2/1993 | Kumada et al. | 324/663 |
| 5,208,544 | 5/1993 | McBrearty et al. | 324/687 |
| 5,239,860 | 8/1993 | Harris et al. | 73/61.48 |
| 5,255,656 | 10/1993 | Rader et al. | 123/494 |
| 5,260,665 | 11/1993 | Goldberg et al. | 324/636 |
| 5,266,899 | 11/1993 | Bull et al. | 324/439 |
| 5,289,132 | 2/1994 | Oksman et al. | 324/439 X |
| 5,296,843 | 3/1994 | Wohlstein et al. | 340/603 |

*Primary Examiner*—Kenneth A. Wieder
*Assistant Examiner*—Jose M. Solis
*Attorney, Agent, or Firm*—Bielen, Peterson & Lampe

[57] ABSTRACT

An apparatus for identifying components associated with the liquid in an electrically non-conductive container utilizing a pair of electrodes. The container extends along a particular dimension such that the first electrode is placed adjacent the exterior of the container and at least a second electrode is placed adjacent the exterior of the container in spaced configuration from the first electrode and along the particular dimension of the container. A generated output signal is coupled into the liquid via the first electrode. The output signal is coupled to the second electrode after passing through the liquid component. The output waveforms are analyzed to determine the electrical characteristics of the liquid in order to identify a component within the container.

13 Claims, 7 Drawing Sheets

RESONANCE CIRCUITS

AMPLIFYING MEANS-36,38

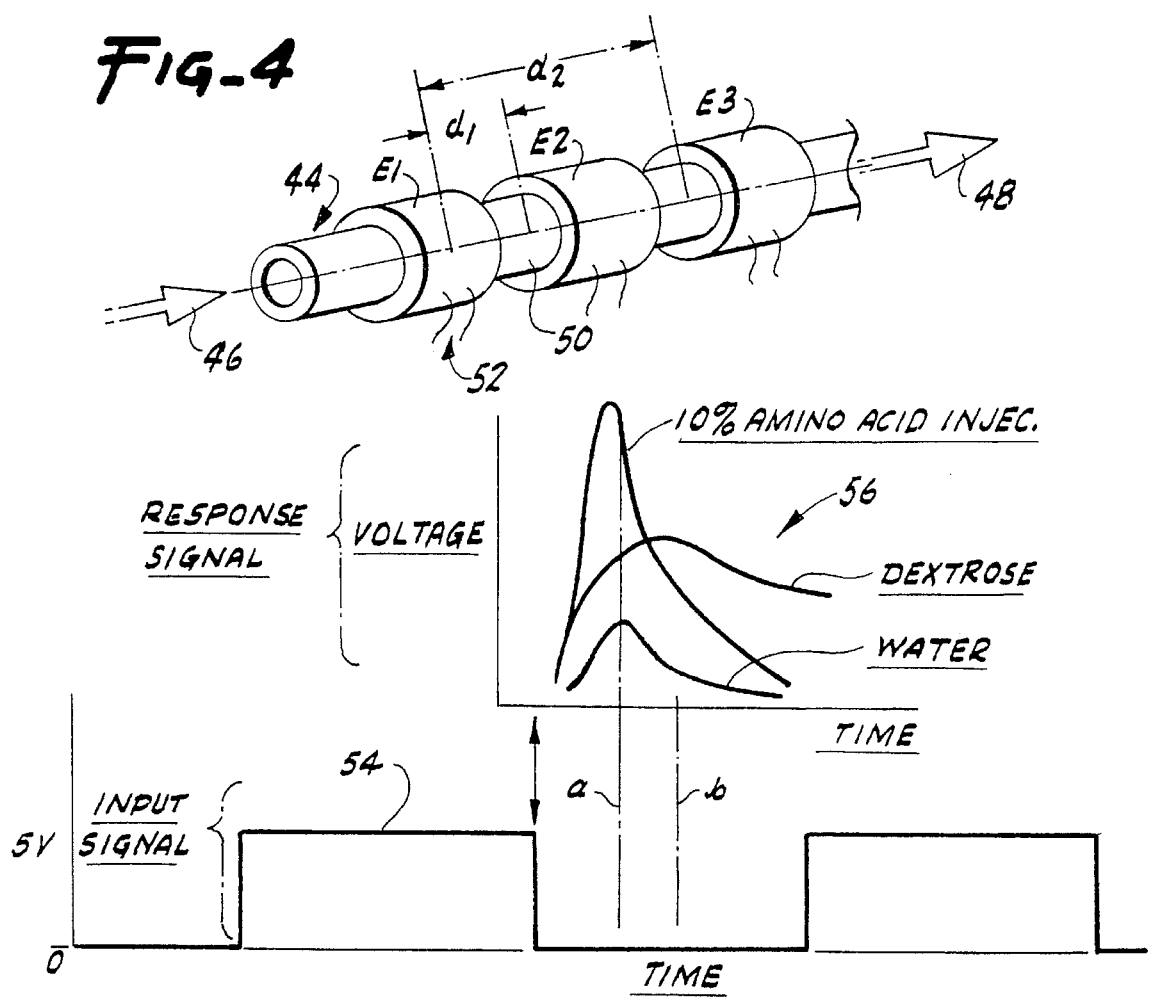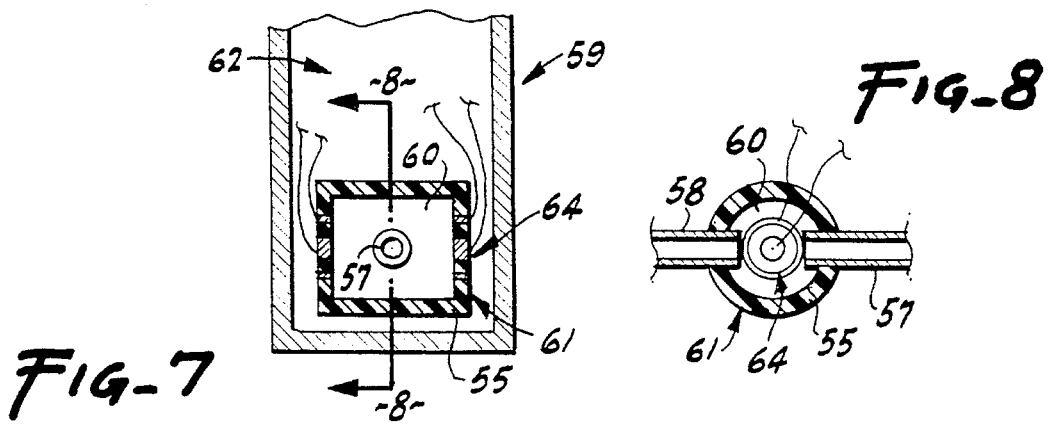

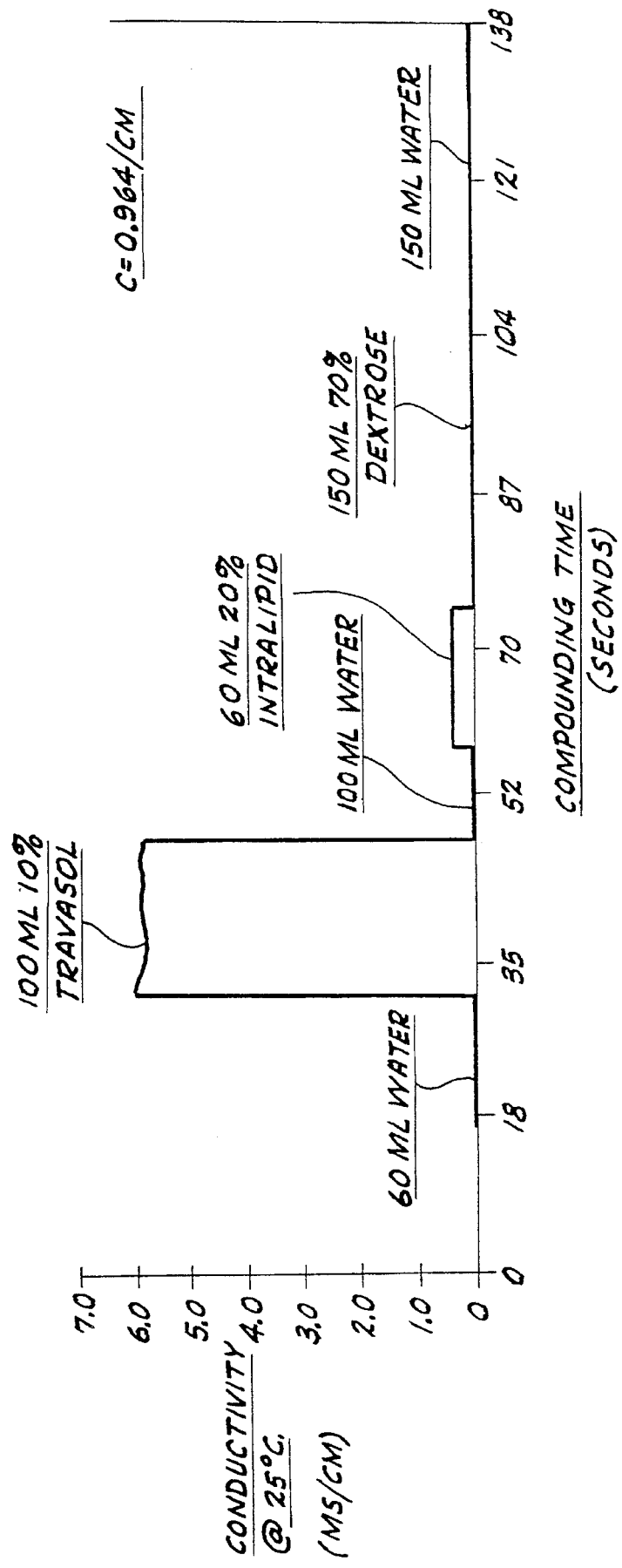

APPARATUS FOR IDENTIFYING PARTICULAR ENTITIES IN A LIQUID USING ELECTRICAL CONDUCTIVITY CHARACTERISTICS

BACKGROUND OF THE INVENTION

The present invention relates to a novel and useful apparatus for non-invasively identifying components associated with a liquid within a container.

Chemical entities are often stored and transported in a liquid medium by containers and conduits. For example, medical solutions such as enteral, parenteral, and other nutrients are compounded or mixed in an intravenous bag fed by separate tubes leading from pure sources of material. In particular, 70% dextrose injection U.S.P., 10% Travasol (amino acid injection), Intralipid 20% I.V. Lipid emulsion, sterile water, potassium chloride, and the like are combined in this manner. Many systems have been proposed to determine the identity of components associated with a liquid passing through a tube or lying in a container using electrical characteristics of the particular component within the tube. For example, such systems are generally invasive, in that the particular probe or electrode of a probe contacts the fluid within the container or tube. Invasive measurements of this type are not acceptable in certain applications such as medical fluids which are intravenously delivered to a patient.

For example, U.S. Pat. No. 3,774,238 describes an invasive measurement of pipeline material utilizing three capacitors to determine dielectric properties of the material.

U.S. Pat. No. 4,074,184 employs invasive capacitance measurements of non-conductive fluids in a tube to determine the vapor-liquid phase ratio.

U.S. Pat. No. 4,227,151 shows an invasive measuring cell for use in determining the electrical conductivity of fluids in a container.

U.S. Pat. No. 4,924,702 describes invasive capacitance sensors that determine the liquid level of a container.

U.S. Pat. No. 4,928,065 shows an invasive measuring apparatus which provides an electrical field from electrodes to determine the characteristics of non-aqueous low conductivity suspensions.

U.S. Pat. No. 4,935,207 employs an invasive capacitive sensor which detects analyte ions in a liquid container.

U.S. Pat. No. 5,068,617 teaches an invasive capacitive device which measures the mixing ratios of composite liquids within a container.

U.S. Pat. No. 5,208,544 describes an invasive sensor which produces dielectric measurements on high temperature molten polymer compositions flowing in a conduit.

U.S. Pat. No. 5,255,656 delineates an electronic sensor which invasively measures the methanol-gasoline mixture in a fuel line by the use of capacitive elements.

U.S. Pat. No. 5,266,899 discloses an invasive salt analyzer which measures the conductivity of saline solutions by inductive non-contact.

U.S. Pat. No. 5,296,843 shows a fluid or vapor diagnostic device employing an invasive probe which generates a light beam passed through a container to a detector to determine the vapor-liquid ratio within that container.

Several systems have been proposed which non-invasively determine the characteristics of fluid in a conduit or container. For example, U.S. Pat. No. 5,239,860 utilizes a light beam which is sent through a tube and detected after interaction with a gasoline alcohol mixture. The wavelength transmission characteristics then determine the actual alcohol-gasoline mixture within the tube.

U.S. Pat. No. 5,260,665 utilizes a non-invasive resonance cell with a pair of probes located therewithin to determine the presence of bubbles within the fluid line passing through the resonance cavity.

An apparatus which is capable of non-invasively identifying components in a container using the electrical conductivity characteristics of the fluid therewithin would be a notable advance in the medical field.

SUMMARY OF THE INVENTION

A novel and useful apparatus and method for non-invasively identifying components in a container are herein provided.

The apparatus and process of the present invention are particularly useful in identifying components associated with a liquid in an electrically non-conductive container such as a tube. The apparatus includes at least a pair of electrodes which are placed adjacent the exterior of the container and positioned in spaced configuration from one another along a dimension of the container. In the case of an elongated flow conduit, such dimension would be the length of such elongated conduit. The first electrode connects to signal means for generating an input waveform. The second electrode spaced along the dimension of the container would serve as a receiving or acquiring electrode which out couples the electrical signal after interaction with the components associated with the liquid in the container. In certain cases, multiple receiving electrodes may be employed along the container to ascertain the waveform after interaction with the components associated with the liquid in the container, each being positioned at greater and greater distances from the first or signal waveform propagating electrode. In essence, the propagating and receiving electrodes form a capacitive resistive circuit with the dielectric container walls and the liquid in the container. The generated signal is modified by the electrical properties of the fluid within the container including conductance, polarizability, and dielectric constant. The conductance of the intervening solution in the cell or tube is found in the resulting signal at the receiving electrodes spaced from the propagating electrodes along the fluid container. "Conductance" is used herein to mean "electrical conductance". Of course, the resulting signal acquired by the receiving electrodes is also dependant on the specific cell configuration, i.e., the cell constant, which is a function of cell and electrode dimensions. Further, polar or ionic species of fluid contain a charge concentration which may lead to signal variations that permit distinguishing of polar from non-polar compounds, which manifest themselves in different signal profiles on time-voltage plots.

The signal means may further be described as an electrical waveform generator which is employed to drive the propagating electrode. Analyzing means is also used for receiving an output waveform from the receiving electrode or electrodes after interaction of the input waveform with the components within the container. The analyzing means also synchronizes the input and output waveforms by the use of timing means which synchronizes the received signal by the receiving electrodes, specifically, to the waveform generator. Such timing means is also employed to activate the analyzing means. The analyzing means acquires data which may be transformed into voltage quantities representing particular fluids in the container or to construct a time-voltage profile of the particular fluid in the container. Consequently, the peak voltages or time voltage profiles positively identify and quantify the fluid within the container.

The signal means for generating an input waveform may be of a type of exciting voltage known as a step function, i.e., a square wave. Thus, the use of a step function easily transforms into characteristics of the fluid within the container being characterized as a function of voltage with time. Moreover, since the response voltages acquired by the receiving electrodes increase upon excitation, peak, and decay over time, various compounds may be distinguished on this basis. For example, different aqueous solutions were observed to reach a peak voltage at different times after excitation and to possess different decay characteristics.

In addition, separation of the receiving or signal acquiring electrodes from the propagating electrode to predetermined distances generates response waveforms that are further determinative of the identification of the components within the liquid medium in the container. Maximum peak signals acquired with various electrode separation facilitate such distinguishing of various components within the container. Moreover, this arrangement is favorable in high conductivity solutions where the propagated signal is detectable over a greater distance than in solutions of low conductivity.

It may be apparent that a novel and useful apparatus and method for identifying components associated with a liquid in a dielectrical container has been described.

It is therefore an object of the present invention to provide an apparatus and method for identifying components associated with a liquid in a dielectrical container that is capable of operation while such components are flowing within the container.

Another object of the present invention is to provide an apparatus for identifying components associated with a liquid in a dielectric container that is simple to use and is accurate.

Another object of the present invention is to provide an apparatus for identifying components associated with a liquid in a dielectrical container that is non-invasive and may be easily employed with medical solutions such as parenteral, and enteral components.

A further object of the present invention is to provide an apparatus for identifying components associated with a liquid in a dielectrical container that eliminates the danger of erroneously compounding medical solutions.

Yet another object of the present invention is to provide an apparatus for identifying components associated with a liquid in a dielectrical container that is useful in the filling of intravenous containers and may be employed to determine the maximum content of electrolytes therein.

The invention possesses other objects and advantages especially as concerns particular characteristics and features thereof which will become apparent as the specification continues.

BRIEF DESCRIPTION OF THE DRAWINGS

FIG. 4 is an isometric view of a partial mechanical embodiment of the present invention using a single waveform propagating electrode and multiple receiving electrodes on a dielectric conduit.

FIG. 5 is an electrical schematic view indicating exemplary non-invasive conductivity values obtained with the apparatus and method of the present invention depicted in FIGS. 2, 3, 4, 6, and 7.

FIG. 7 is a sectional view of a modified conductivity probe to obtain data described in detail in Example 1 hereinafter.

FIG. 8 is a sectional view taken along line 8—8 of FIG. 7.

FIGS. 9–11 are graphical representations of quantitative analyses conducted utilizing the probe of FIGS. 7 and 8 and described in detail in Example 1.

For a better understanding of the invention reference is made to the following detailed description of the preferred embodiments thereof which should be referenced to the prior described drawings.

DETAILED DESCRIPTION OF THE PREFERRED EMBODIMENTS

Various aspects of the present invention will evolve from the following detailed description of the preferred embodiments thereof which should be taken in conjunction with the prior described drawings.

Figure 3:
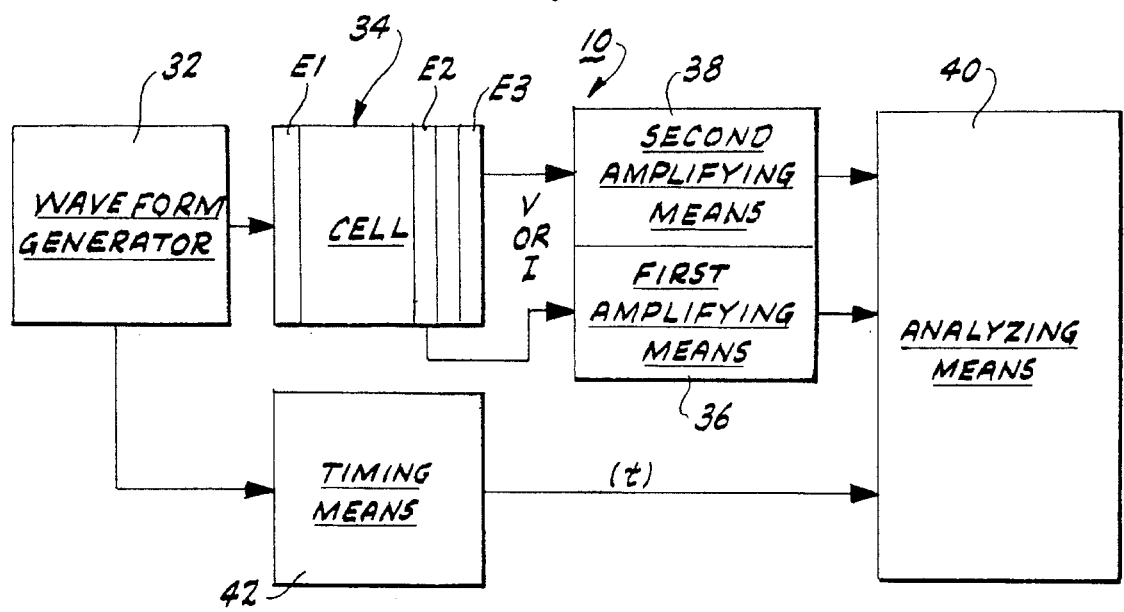
FIG. 3 is a block diagram representative of the overall apparatus and method of the present invention.

The invention as a whole is shown in the drawings by reference character 10 and is depicted schematically in FIG. 3. The apparatus 10 is employed to identify liquid components in a dielectric container such as a tube, vat, and the like. In particular the apparatus and process of the present invention are especially applicable to the detection of parenteral, and enteral components which are employed in the composition of appropriate medical solutions.

Figure 1:
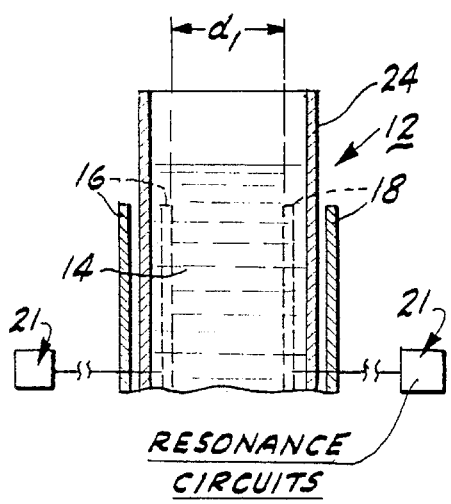
FIG. 1 is a side schematic view of a prior art dielectric cell measuring system.

With respect to FIG. 1, a prior art dielectric cell 12 is depicted and is normally employed to measure the dielectric constant of solution 14 within cell 12. Electrodes 16 and 18 are normally placed outside cell 12. Electrode 16 and electrode 18 form the capacitor in a resonance circuit 21. The resonant frequency of circuit 21 is proportional to the capacitance of opposing electrodes 16 and 18. The frequency of resonance is used to determine the electrical characteristics of solution 14, namely the dielectric constant. Phantom electrodes 16 and 18 have also been placed immediately inside the walls 24 of cell 12 to indicate prior invasive measuring techniques for highly dielectric liquids. Cell 12 characteristics have been determined by measuring the average voltage developed in an R-C circuit with a fixed driving frequency. Cell 12 fails in measuring the dielectric constant of solutions 14 having a high conductivity. This deficiency is believed to be due to the dominance of the conductivity of solution 14. The electrodes 16 and 18 are simply positioned in opposition to one another across cell 12 as depicted in FIG. 1 to form a parallel plate capacitor separated by a distance $d_1$.

Figure 2:
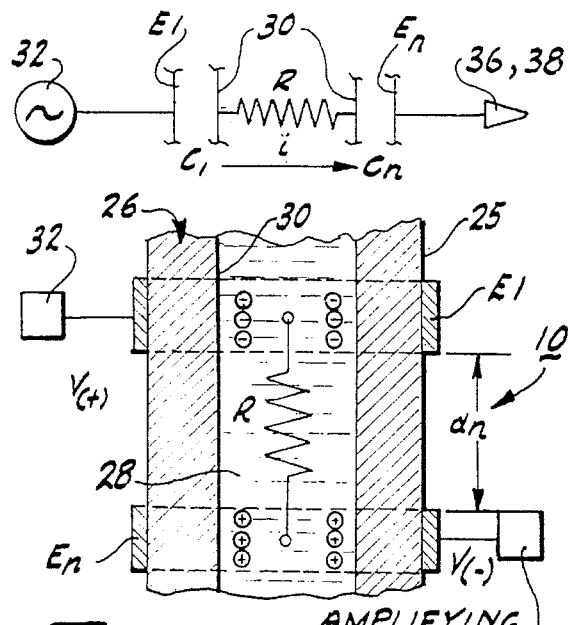
FIG. 2 is a top plan schematic view of the theoretical system of the present invention, depicted mechanically and electrically.

FIG. 2 is a theoretical mechanical and electronic schematic depicting workability of apparatus 10 of the present invention. Electrode E1 propagates a waveform (V+) received from a waveform generator 32. The term "electrode" is employed herein in its broadest sense as an item or element that emits, collects, or controls the movements of electrons. Electrode $E_N$ represents one or more receiving electrodes found on the outside wall 25 of dielectric container 26 depicted schematically in FIG. 2. Electrodes E1 and En couple (primarily by an electric field) or induce (primarily by a magnetic field) the waveform (V+) through the wall 25 of dielectric container 26, and into or from the material or fluid 28 being sensed within dielectric container 26. By placing any of the receiving electrodes En along the outside wall 25 of container 26 (distance $d_1$), rather than across or opposite from one another, cell 12 of FIG. 1, capacitive effects are minimized. Receiving electrodes En may be positioned non-invasively to lie against the outside wall 25 of dielectric container 26 or be embedded within wall 25 of dielectric container 26. In contrast, in the dielectric cell 12 of FIG. 1, the capacitive effects are maximized. Multiple electrodes, En, may be employed in apparatus 10 of the present invention at various distances measured along outside wall 25 of dielectric container 26. In addition, the primary capacitance is related to the electric field from each electrode E1, En to the solution across the outside cell wall 25, depicted schematically in FIG. 2. The charge concentration of sample fluid 28 between inner walls 30 is depicted by the (+) and (−) symbols along the inner wall 30 of dielectric container 26. The resistance of the sample is indicated by "R". In turn, conductance of the intervening sample 28 is represented by the formula:

$$1/R$$

FIG. 2 represents a resistive capacitive circuit with the electrical characteristics modified by the conductance, polarizability, ion mobility, dielectric constant, and other electrical properties of the fluid sample 28 between the dielectric wall portion 30. It should be noted that the resultant signal on electrode $E_N$, indicated at V(−), is dependant on specific cell configuration formed by container 26, as well as the conductance, polarizability, and dielectric constant of the intervening fluid. In essence, FIG. 2 indicates that different signal profiles may be obtained in time-voltage plots using electrodes on the exterior wall 25 of container 26.

Apparatus 10, shown as a functional block diagram in FIG. 3, includes electrical waveform generator 32 which generates a periodic signal that may be sinusoidal, a square wave, a saw tooth, or any modification of the same. Waveform generator 32 passes the waveform signal to propagating electrode E1 around the cell 34. Cell 34 may take the form of a container such as a tube, vat, and the like. Fluid may be flowing through cell 34 or be static therewithin. Although E1 is depicted in singular form, additional propagating electrodes may be employed (not shown) to provide additional electrical shielding or field shaping of the waveform in order to modify the cell constant of cell 34. Collecting, acquiring, or receiving electrodes E2 and E3 are also depicted in FIG. 3. It should be noted that a plurality of such receiving electrodes may be employed in the present apparatus 10. Collecting or receiving electrodes E2 and E3 are spaced from propagating electrode E1 and positioned along a dimension of cell 34. Where cell 34 is a tube, such particular dimension would be the length of that tube, which will be shown in detail hereinafter. After modification by the components associated with a liquid within cell 34, the output waveform (current (I) or voltage (V)) received by electrodes E2 and E3 is passed to first and second amplifying means 36 and 38. The output of amplifying means 36 and 38 are passed to analyzing means 40 in the form of a signal which may be a voltage. Timing means 42 synchronizes the output of waveform generator 32 and the input from first and second amplifying means 36 and 38 to analyzing means 40. Timing means 42 also activates analyzing means 40. The timing means signal is indicated by "t" in FIG. 3. Analyzing means 40 processes the timing signal and the voltage outputs of first and second amplifying means 36 and 38 are representative of the particular fluid in capacitive cell 34 between propagating electrode E1 and E2 or E3. Thus, a voltage-time profile of the fluid in the cell may be plotted to positively identify and quantify a particular component of fluid sample 28. Such identification is especially important with medical solutions.

Referring to FIG. 4, it may be observed that a dielectric tube 44 is employed to conduct fluid therethrough according to directional arrows 46 and 48, although fluid may flow in the opposite direction. Propagating electrode E1 and receiving electrodes E2 and E3 are shown adjacent outer wall 50 of tube 44. Of course, other receiving electrodes may be used in addition to electrodes E2 and E3 in this regard. Electrodes E1, E2, and E3 are generally formed of metallic material such as stainless steel and include a plurality of electrical conductors 52 shown schematically in FIG. 4. It should be realized that electrodes E1 and E2 are separated from one another along tube 44 at a distance d1. Also, electrode E1 and E3 are separated by a distance d2. The significance of this separation will be discussed in detail hereinafter and illustrated in the subsequent examples.

The form of the exciting voltage from waveform generator 32 is preferably a periodic wave and may be a "step" function, such as a square wave. By utilizing a step function as the source, it has been found that the characteristics of the intervening fluid within cell 34 can be described above as a function of voltage and time. With reference to FIG. 5, this phenomena is exemplified where an input square wave 54 is sent to electrode E1 of FIG. 4. The response signals for 10% amino acid injection, dextrose, and water are depicted in graph 56, FIG. 5. Response voltages shown in graph 56 rapidly increase upon excitation by input signal 54, while peak and decay vary over time depending on the particular component being present in capacitive cell 34, FIG. 3. For example, the values for amino acid injection, dextrose, and water, are quite different at time point "a" and time point "b". In other words, the analyzing means detection electronics looks at the amplitude of a response voltage versus time at a particular time or the average response voltage over an interval of time. In either case, compounds present in cell 34 are easily distinguishable. Moreover, in graph 56 of FIG. 5, amino acid injection reached a maximum peak intensity at approximately (100) nanoseconds prior to the dextrose solution. However, dextrose exhibited a much slower signal increase and decay than 10% amino acid injection. Thus, a different response signal result is attained at time instants "a" and "b". It has been found that a square wave input signal 54 at about 200 kilohertz possesses sufficient speed to characterize differences in the response of components of FIG. 5 (5–10 microsecond response time). In other words, input signal rise times of between (10) nanoseconds and several microseconds are sufficient to distinguish most responses in common parenteral nutrients, trace element solutions, and various electrolytes, depending on cell configuration. In addition, a capacitively coupled periodic signal such as square wave input 54 is also helpful in minimizing long term ion migration and concentration gradients at or near electrodes E1, E2, and E3. Thus, instability or drift of the response signal over time is greatly minimized. It should be understood that other periodic waveforms generated by waveform generator 32 may be employed to enhance the results depicted in FIG. 5. For example, a ramp waveform, an integral of a ramp waveform, and the like may be employed in this regard.

Figure 6:
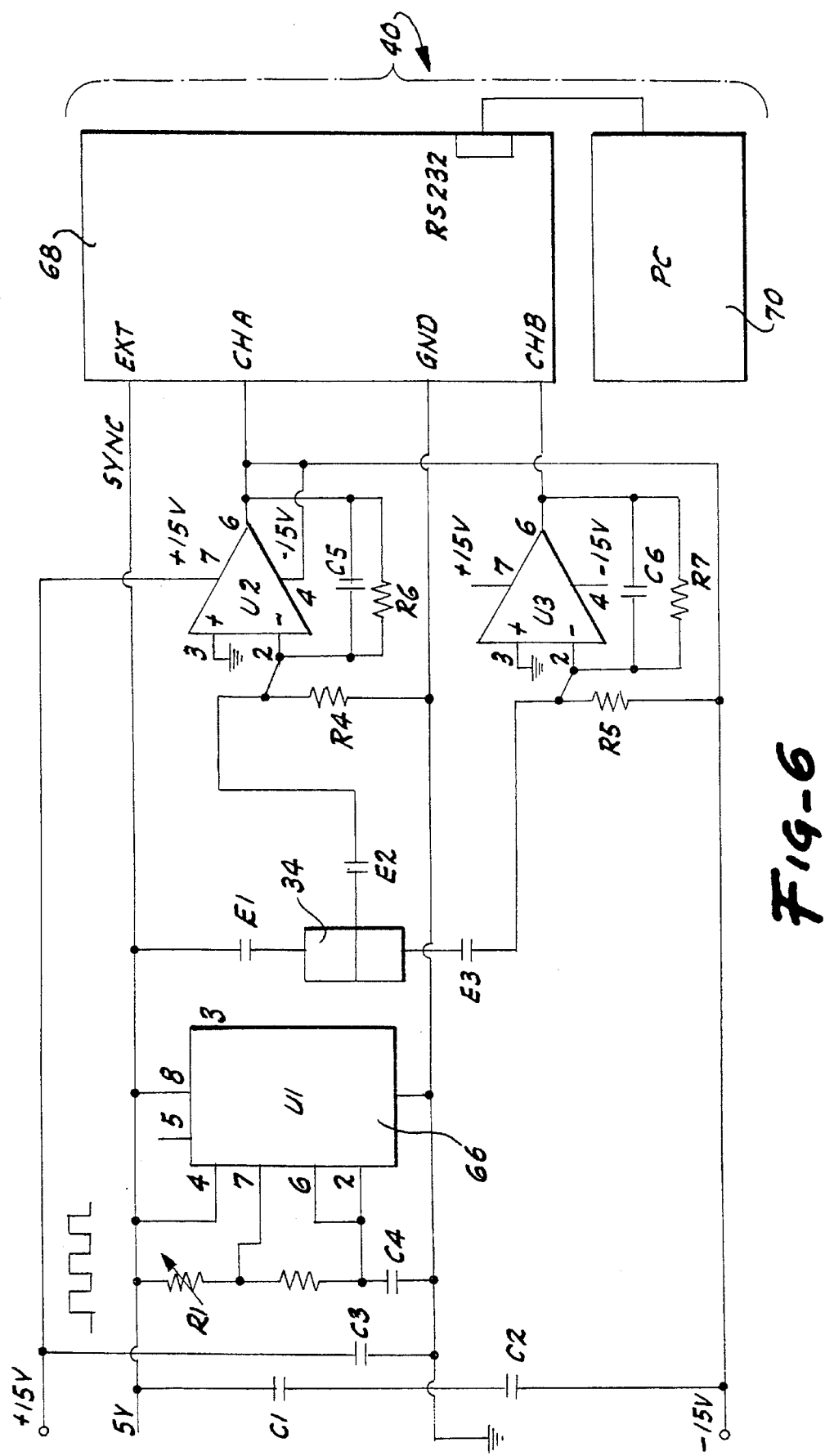
FIG. 6 is an electrical schematic diagram of the circuitry employed in the present invention.

FIG. 6 represents the electrical schematic of the signal acquiring circuit used in the apparatus 10 of the present invention. An IC timer U1, generates an input square wave. C1, C2, and C3 operate as power supply filters to bypass noise. Integrated circuit (IC) timer U1 is configured for stable operation as oscillator 66. R1, R2, and C4 are selected to generate a near 50% duty cycle square wave on pin 3 of U1. R3 provides additional source drive capability for U1. Cell or tube 34 containing a component to be analyzed, is surrounded in the configuration depicted in FIG. 4 by electrodes E1, E2, and E3. Signal propagating electrode E1 sends the waveform from oscillator 66 through the components found in cell 34. Acquiring electrodes E2 and E3 pass the output signal to amplifiers U2 and U3, respectively. U2 is a transimpedance amplifier (current to voltage). Gain and response times are determined by R6 and C5. The RC constant for these components is 0.44 micro seconds. R4 is a high impedance ground bias for the capacitively coupled E2 input to U2. The output of U2 is sent to oscilloscope 68 and from there to computer 70 via an RS232 link. Computer 70 may be an IBM PC/486 DX2-66 with 8 megabytes RAM and a grams/386, version 3.01B, level 12 program, available from Galactic Industries of Salem, N.H. Transimpedance amplifier U3, receiving the output from electrode E3, performs a similar function with respect to U2 by inputing oscilloscope 68. R5, C6, and R7 are analogous to the R4, C5, and R6 components with respect to amplifier U2.

The following list represents components employed in FIG. 6.

| LIST OF COMPONENTS | | |
|---|---|---|
| Item | Designation | Source |
| C1 | 0.1 Micro F | M.1. Std. CK05BX 104K 50V |
| C2 | 0.1 Micro F | M.1. Std. CK05BX 104K 50V |
| C3 | 0.1 Micro F - Series | M.1. Std. CK05BX 104K 50V |
| C4 | 100 pF - C114 Kemet | M.1. Std. CK05BX 104K 50V |
| C5 | 2 pF | Kemet Electronics Corp. Greenville, SC |
| C6 | 2 pF | Kemet Electronics Corp. Greenville, SC |
| R1 | 15 kOhm RN55D Series | Dale Electronics (VISHAY) Columbus, NE |
| R2 | 1 kohm | Dale Electronics (VISHAY) Columbus, NE |
| R3 | 1 KOhm | Dale Electronics (VISHAY) Columbus, NE |
| R4 | 10 MOhm | Dale Electronics (VISHAY) Columbus, NE |
| R5 | 10 MOhm | Dale Electronics (VISHAY) Columbus, NE |
| R6 | 220 k Ohm | Dale Electronics (VISHAY) Columbus, NE |
| R7 | 220 k Ohm | Dale Electronics (VISHAY) Columbus, NE |
| U-1 (66) | 555 Timer | Texas Instruments, Dallas, TX |
| U-2 (36) | OP Amp 843 | Analog Device, Norwood MA |
| U-3 (38) | OP Amp 843 | Analog Device, Norwood MA |
| Oscilloscope 68 | Model 97 | Fluke, Inc., Everette, WA |
| Computer 70 | PC/386 w/RS232 | |

In operation, apparatus 10 determines the presence of a component flowing or statically present within a container, such as dielectric tube 44, by placing a first electrode E1 adjacent the exterior surface 50 of tube 44. Additionally, electrodes E2 and E3 are also fastened adjacent the exterior 50 of tube 44, but are spaced from one another and spaced from electrode E1 along tube 44. Such spacing occurs along a particular dimension such as the length of tube 44. For example, electrodes E1, E2, and E3 are typically (10–13) mm long for a (4) mm OD tube and spaced at 10–13 mm intervals. With respect to the schematic shown in FIG. 6, a waveform is generated by oscillator 32, 66 and fed, using the circuitry of FIG. 6, to propagating electrode E1. After interaction with the components within tube 44, electrodes E2 and E3 acquire the signal and pass the same to analyzing means 40 in the form of oscilloscope 68 and personal computer 70 via RS232 communications. Oscilloscope 68 indicates a characteristic output signal per unit time. Time voltage points are queried by computer 70 to oscillator 66 via the RS232 of computer 70. A software program in computer 70 determines a characteristic, such as conductivity of a component within tube 44. Timing means 42 such as timer U1, FIG. 6, generates the signal to be used to trigger (synchronize) signals to produce further distinguishing characteristics of the acquired signal along a certain time span. Components or materials within tube 44 are easily identified by comparison of signal characteristics determined by both time and distance signals measured, as modified by the material's electrical characteristics.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

The following examples are included for the purposes of illustration, but are not intended to limit the scope of the invention unless otherwise indicated.

EXAMPLE I—INVASIVE CONDUCTIVITY

Invasive conductivity measurements using the following procedure were conducted in order to ascertain whether direct contact conductivity measurements could be used to identify different parenteral nutrients normally available in a compounding process. A conductivity meter, Orion Model 126, with a modified Orion probe 012210, manufactured by Orion, Inc., Boston, Mass., was employed to measure the conductivity and to identify different parenteral nutrients during compounding using a commercial compounder. The probe employed had a thermocouple for accurate temperature compensation and a four graphite electrode design to eliminate any polarization effects with a cell constant of 0.69/cm. With reference to FIGS. 7 and 8, probe 59 was modified by inserting PVC tube 55 to form container 61. PVC tubes 57 and 58 were inserted within the cylindrical cavity 60 of container 61. The solution to be analyzed was passed into and held within the cavity or chamber 60, allowing fluid contact with the concentric Orion probe electrodes 64. This procedure decreased the volume of container 61 and reduced the mixing time of the sample within chamber 60 in contact with the electrodes 64. Container 61 possessed a cell constant of 0.964. In such configuration, the thermocouple was not in contact with the liquid being tested.

Table I represents the data obtained in this example.

TABLE I

| ITEM | CONDUCTIVITY, mS/cm @ 25° C. (cell constant = 0.94/cm) |
|---|---|
| 10% Travasol (Amino Acid) Injection | 6.63 |
| 70% Dextrose Injection USP | 0.02 |
| Sterile Water | 0.00 |
| Intralipid 20% I.V. Fat Emulsion | 0.43 |
| 8.5% Travasol (Amino Acid) Injection | 5.02 |
| 10% FreAmine III** Amino Acid Injection | 5.32 |
| 10% Aminocyn Amino Acid Injection | 5.67 |
| 6% TrophAmine Amino Acid Injection | 4.21 |
| Potassium Phosphates Injection USP; 3 mM/ml P, 4.4. mEq/ml K | 150.80 |
| MVI Pediatric Vitamins | 0.20 |
| Heparin Sodium Injection USP; 1000 USP Units/ml | 7.42 |
| Zinc Sulfate Injection USP; 1 mg Zn/ml | 3.07 |
| MTE-5 Trace Element Mixture | 8.92 |
| Potassium Chloride Injection Concentrate USP; 2 mEq/ml | 210.00 |
| Calcium Gluconate Injection USP | 5.53 |
| Potassium Acetate Injection USP; 4 mEq.ml | 146.40 |
| Lypholyte Multi-Electrolyte Concentrate | 143.10 |
| Sodium Acetate Injection USP; 4 mEq/ml | 74.60 |

A dynamic test was performed with a commercial compounder where individual tubes were connected to multiple starting solution bottles and then combined into one tube at a junction or manifold. Peristaltic pumps forced the starting solutions through the manifold and into container 61 via tube 57. The solutions tested included sterile water, 70% Dextrose injection, 10% amino acid injection solution, and 20% lipid emulsion. Normally the outlet PVC tube 58 would have led to an intravenous bag, but in the present example, probes 64 were inserted within cylindrical cavity 60 between the junction or manifold of the compounder and the place where the PVC tube 58 connected to the final container (IV bag). The conductivity meter was set to manual scaling and the analog voltage output was connected to an analog-to-digital board in a personal computer. The resulting counts were recorded as a function of compounding time, transferred to a computer spreadsheet program, and plotted.

Figure 11:
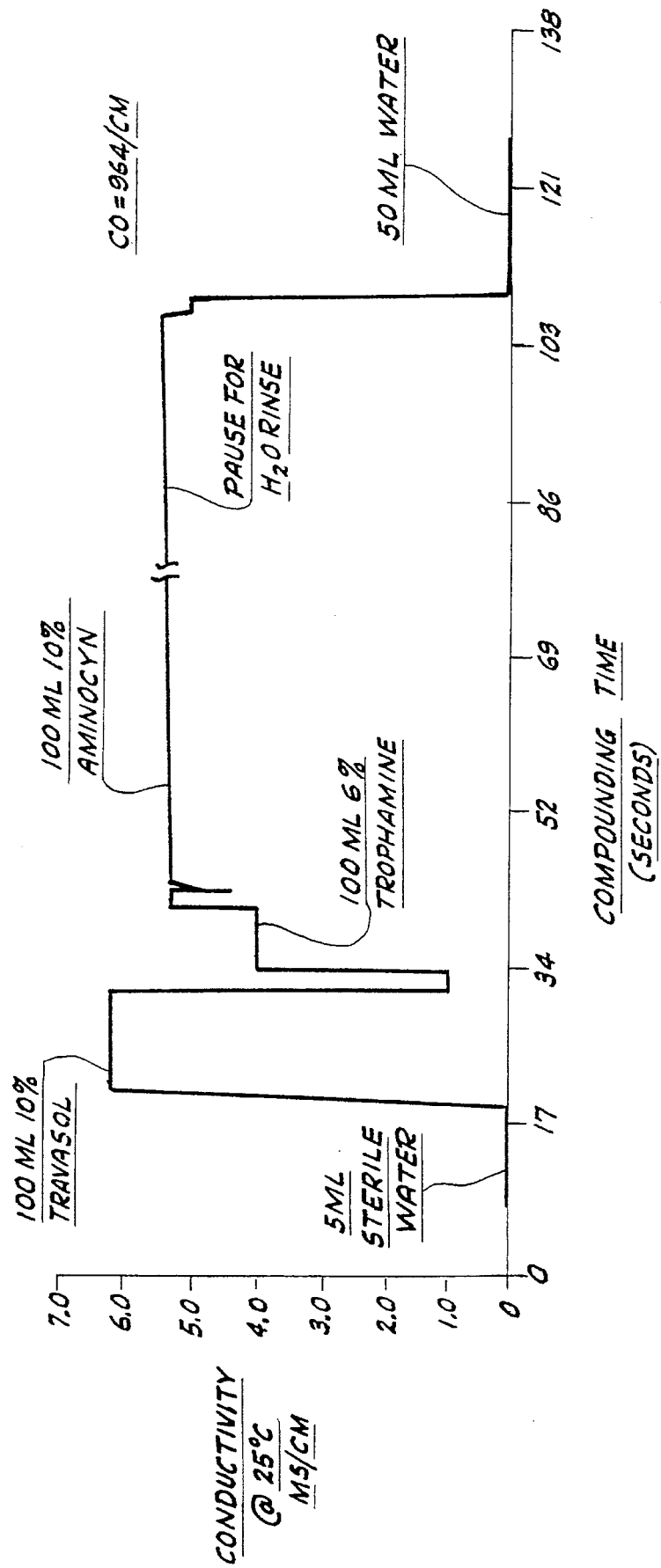

With reference to FIG. 9, a distinction was detected between amino acid and lipid solutions. Water and dextrose, having much lower conductivities were not identifiable on the plot of FIG. 9. The compounding time plotted against measured conductivity on FIG. 9 also included the volume of each solution pumped through the compounder. With reference to FIG. 10, a finer conductivity scale was employed and illustrated a measurable distinction between sterile water and 70% dextrose solution. It is believed that the large spike in conductivity at the beginning of the plot of FIG. 10 was due to the expulsion of previously existing amino acid in the compounder tubing 58. Referring to FIG. 11, different amino acid injection solutions were shown to be distinguishable. It is also noted that gas bubbles transferring through the tubing were plotted as a sharp decrease in conductivity. It was concluded that direct contact measurements of electrical conductivity of compounds can be used to identify them during the compounding process.

EXAMPLE 2—NON-INVASIVE CAPACITIVE MEASUREMENTS

Solutions were contained in poly-vinyl chloride/PV Acetate tubing of the type typically used in commercial compounders having an outer diameter of about 6.35 millimeters and a wall thickness of about 0.9 millimeters. Static measurements were made on these tubes and used to positively identify several major nutrients with a commercial compounder under flow conditions. FIG. 4 represents a portion of the apparatus employed in this example. The propagating electrode E1 and acquiring electrodes E2 and E3 were formed of conductive tapes, available from 3M Co., St. Paul, Minn. The conductive tapes had a width of 12.7 millimeters and a thickness of about 0.075 millimeters. The conductive tapes were placed completely around the tubing such as tubing 44 of FIG. 4, and were spaced 13 millimeters apart. These tapes rested in aluminum holders machined in a shape that conformed to the exterior surface of the tubing. A square wave signal was generated with a frequency of about 220 kHz for the following measurements. This frequency was chosen because good distinction among compounds tested was obtained, although other frequencies were used as well. Means for sampling and holding and means for averaging was employed in the electronic circuit, i.e., analyzing means 40 of FIG. 6. A response signal received by one acquiring electrode formed of the conductive tape was sent to an analog-to-digital (A/D) converter, which in turn was connected to the parallel port of a personal computer. A computer program was written to acquire the signal from the A/D converter, to display its value, and to identify a particular chemical entity found in the exit tube from the compounder. Such computer program is included as an appendix hereto. Table II represents the values for certain parenteral nutrients which was determined by the above method and apparatus. It should be noted that there were 2.44 millivolts per (A/D) count in Table II. As may be seen, the values obtained indicate that individual compounds may be easily distinguished. Furthermore, it was found that the absence of a liquid compound in a tube could also be detected relative to an full tube. 70% dextrose is associated with a test count of 260, while sterile water was associated with 130 counts. This difference indicates that other dextrose solutions such as 35% dextrose should be readily distinguishable also from sterile water. It was also determined that errors of mistakenly switching water and dextrose tubes on a compounder should immediately be identified with the invention shown. FIGS. 2–4 represent the mechanical, electronic, and schematic definition of the device employed in the present example.

TABLE II

NON-INVASIVE CAPACITIVE COUPLED TEST VALUES

| Compound | Counts |
| --- | --- |
| No tube present | 0 |
| Empty tube present | 10 |
| Sterile Water | 130 |
| 70% Dextrose Injection | 260 |
| 10% Amino Acid Injection | 350 |
| 20% Lipid Emulsion | 680 |

EXAMPLE 3—NON-INVASIVE CAPACITIVE COUPLED MEASUREMENTS USING FULL PEAK PROFILE AND MULTIPLE ACQUIRING ELECTRODES

Figure 12:
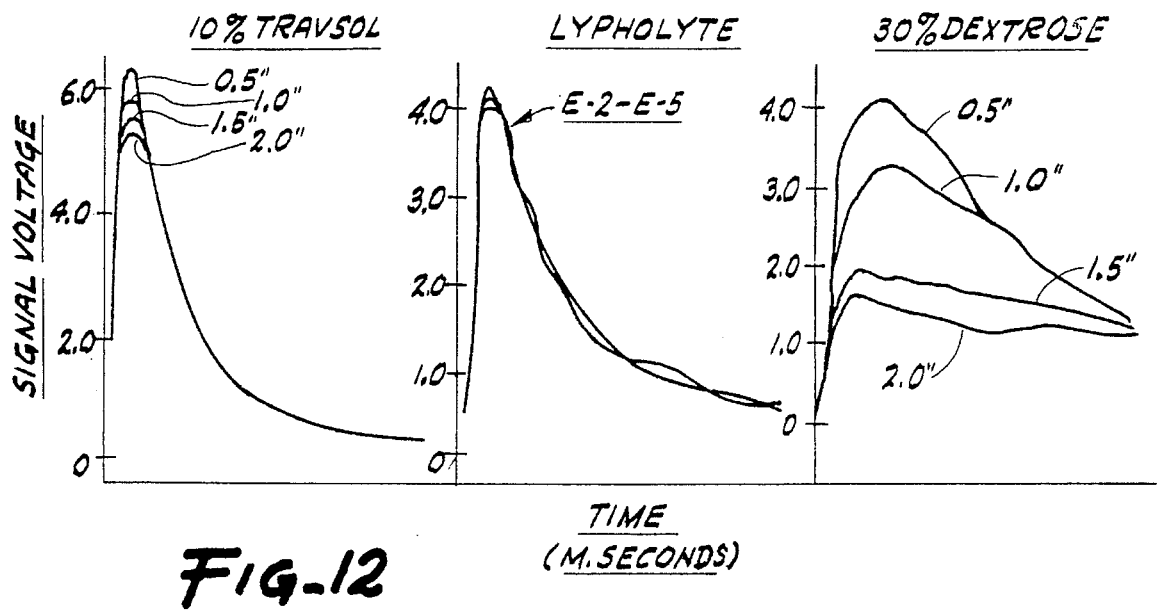
FIGS. 12 and 13 represent analytical results delineated in Example 3.
Figure 13:
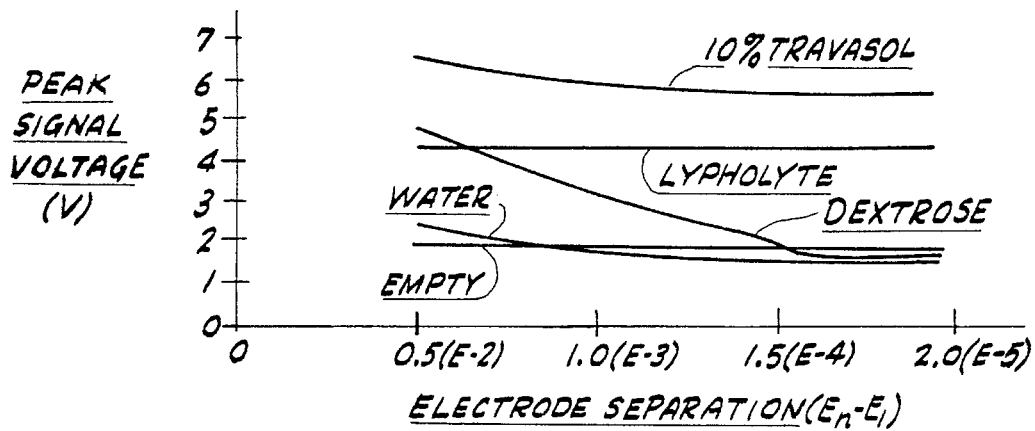

The electrodes such as those depicted in FIG. 4, with the addition of electrodes E4 and E5 (not shown) identical to electrode E2 were employed with the circuit shown in FIG. 6. A modified square wave input signal was used as the waveform sent to electrode E1 through timer integrated circuit U1. The input signal had a period near 220 kHz. An electrodes E2 was successively placed at 0.5 (12.7 mm) inch intervals along a (3) millimeter inner diameter polyvinyl chloride (PVC) tube connected to an intravenous bag. Such placements are depicted as E2, E3, E4, and E5. The electrodes were fitted snugly over the exterior surface of the polyvinyl chloride tube. Each electrode, E1 and E2, was 0.5 inches wide and was connected to the circuit depicted in FIG. 6. The square waveform input was generated and transmitted from the 555 oscillator, through the tube and solution contained in the tube to electrode E2–E5, the acquiring electrodes. The response waveforms were then amplified, acquired and measured by an oscilloscope, a Scopemeter 97 manufactured by Fluke, Inc. of Everett, Wash., i.e., triggered to synchronize to the input waveform. The acquired signal was then fed to the serial port of a computer and collected for analysis using the Grams/386 Level II software program, manufactured by Galactic Industries of Salem, Me. The input and output or response waveforms were collected from the oscilloscope. A commercial compounder for parenteral nutrients, i.e., a compounder, manufactured by Clintec Nutrition Company under the trademark Automix 3-3, of Deerfield, Ill., was used to transfer approximately 60 milliliters of solution from source containers to the intravenous bag via the polyvinyl chloride tube. Waveforms were collected during the pumping cycle. FIG. 12 represents the characteristic response waveforms for 10% Travasol, Lypholyte, and 30% dextrose, three common parenteral nutrients. Response waveforms shown in FIG. 12 for each nutrient spans about 2.2 microseconds. The vertical axis represents signal voltage in volts. Each of the three nutrients was determined to have a characteristic response profile reaching maximum signal quickly and decaying over time. The distances shown on the graph of FIG. 12 represents electrode separation between the waveform propagating electrode E1 and a single electrode E2. The 30% dextrose injection solution exhibited a broader maximum voltage, reaches such maximum voltage later than 10% Travasol or Lypholyte peak measurements, and decays more slowly over time. The 10% Travasol injection solution exhibited a narrower peak at an earlier time than the peaks reached by the dextrose solution. In addition, 10% Travasol decayed more quickly than dextrose. Moreover, 10% Travasol exhibited less variation of peak voltage for changes in E1–E2 distances than dextrose. Lypholyte, a mixture of electrolytes, showed a similar response to 10% Travasol, but with a lower maximum signal and very little peak voltage variation with changes in the E1–E2 electrode distance. FIG. 13 depicts a change in maximum peak signals of the nutrients plotted in FIG. 12 using propagating electrodes and acquiring electrodes E1, E2, and the designations E3, E4, and E5 representing different distance intervals of E2 from E1. Thus, the 10% Travasol and Lypholyte may be distinguished by combining the results of FIGS. 12 and 13. It was concluded that adding a second or several additional receiving or signal acquiring electrodes such as E2, further distinguished solutions passing through the polyvinyl chloride tube.

What is claimed is:

1. An apparatus for identifying components associated with a liquid within a dielectric container comprising:
   a. a first electrode placed apart from contact with the liquid and adjacent the exterior of the dielectric container;
   b. a second electrode placed apart from contact with the liquid and adjacent the exterior of the dielectric container, said second electrode positioned in spaced configuration from said first electrode along the outer surface of the container;
   c. signal means for generating an input waveform, said signal means being electrically connected to said first electrode, and
   d. analyzing means for receiving an output waveform from said second electrode after interaction of said input waveform with the components within the container, said analyzing means further including indicating means for correlating said output waveform to the presence of particular components in the container, dependent on the electrical conductivity of the particular components associated with a liquid within the container, said analyzing means further including timing means linked to said signal means for synchronizing said signal means with said analyzing means.

2. The apparatus of claim 1 in which said input waveform is a periodic wave.

3. The apparatus of claim 1 in which said input waveform is a square wave.

4. The apparatus of claim 1 in which said input waveform is a modified square wave with controlled rise and fall characteristics.

5. The apparatus of claim 1 which additionally comprises a third electrode placed apart from contact with the liquid and at the exterior of the container, said third electrode being further positioned in spaced configuration from said first electrode along the particular dimension of the container at a distance greater than said distance of said second electrode from said first electrode, and said analyzing means being capable of receiving an output waveform from said third electrode after interaction of said input waveform with the component within the container, and said indicating means further correlating said output waveform received from said third electrode to the presence of a particular component in the container.

6. The apparatus of claim 1 in which said first and second electrodes each at least partially circumvent the container.

7. The apparatus of claim 1 in which said first and second and third electrodes each at least partially circumvent the container.

8. An apparatus for identifying the presence of a liquid in a dielectric transfer tube comprising:

a. a first electrode placed adjacent the exterior of the container;

b. a second electrode placed adjacent the exterior of the container and positioned in spaced configuration from said first electrode along the outer surface of the container;

c. signal means for generating an input waveform, said signal means being electrically connected to said first electrode; and d. analyzing means for receiving an output waveform from said second electrode after interaction of said input waveform with the components within the container, and comparing said input and output waveforms, said analyzing means further including indicating means for correlating said output waveform to the presence of particular components in the container, said analyzing means further including timing means linked to said signal means for synchronizing said signal means with said analyzing means.

9. The apparatus of claim 1 in which said input waveform is a periodic wave and in which said first and second electrodes circumvent the container.

10. A method of determining the presence of a component associated with a liquid in a dielectric container comprising:

a. placing a first electrode adjacent the exterior of the container;

b. placing at least a second electrode adjacent the exterior of the container at a position in spaced configuration from said first electrode along the particular dimension of the outer surface of the container;

c. generating an input waveform and feeding said input waveform to said first electrode;

d. analyzing an output waveform from the second electrode after interaction of the input waveform with a component within the container to determine an electrical characteristic indicating the presence of a particular component in the container, said step of analyzing an output waveform including the step of providing timing means linked to said signal means for synchronizing said signal means with said analyzing means.

11. The method of claim 10 which additionally comprises the steps of placing a third electrode adjacent the exterior of the container in spaced configuration from said first electrode along the particular dimension of the container at a distance greater than said distance of said second electrode from said first electrode, and analyzing an output waveform from the third electrode after interaction of the input waveform with a component within the container to determine an electrical characteristic indicating the presence of a particular component in the container.

12. The method of claim 11 which additionally comprises the step of comparing the output waveform of said second and third electrodes.

13. An apparatus for identifying parenteral and enteral nutrients, comprising:

a. a first electrode placed adjacent the exterior of the container;

b. a second electrode placed adjacent the exterior of the container and positioned in spaced configuration from said first electrode along the outer surface of the container;

c. signal means for generating an input waveform, said signal means being electrically connected to said first electrode; and d. analyzing means for receiving an output waveform from said second electrode after interaction of said input waveform with the components within the container, and comparing said input and output waveforms, said analyzing means further including indicating means for correlating said output waveform to the presence of particular components in the container said analyzing means further including timing means linked to said signal means for synchronizing said signal means with said analyzing means.

* * * * *